United States Patent
Cummins et al.

(10) Patent No.: US 9,750,786 B2
(45) Date of Patent: *Sep. 5, 2017

(54) TREATMENT OF THROMBOCYTOPENIA USING ORALLY ADMINISTERED INTERFERON

(71) Applicant: AMARILLO BIOSCIENCES, INC., Amarillo, TX (US)

(72) Inventors: Martin Joseph Cummins, Georgetown, TX (US); Chau-Ting Yeh, Lu-Chu Xiang (TW); Ching-Yuan Lee, Bao-shan Xiang (TW)

(73) Assignee: Amarillo Biosciences, Inc., Amarillo, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/338,772

(22) Filed: Oct. 31, 2016

(65) Prior Publication Data

US 2017/0042974 A1    Feb. 16, 2017

Related U.S. Application Data

(63) Continuation of application No. 14/398,647, filed as application No. PCT/US2013/038785 on Apr. 30, 2013, now Pat. No. 9,526,694.

(60) Provisional application No. 61/642,208, filed on May 3, 2012.

(51) Int. Cl.
  A61K 9/00    (2006.01)
  A61K 38/21   (2006.01)

(52) U.S. Cl.
  CPC ............ *A61K 38/212* (2013.01); *A61K 9/006* (2013.01); *A61K 9/007* (2013.01); *A61K 9/0056* (2013.01); *A61K 9/0078* (2013.01); *A61K 38/21* (2013.01)

(58) Field of Classification Search
  None
  See application file for complete search history.

(56) References Cited

U.S. PATENT DOCUMENTS

| | | | |
|---|---|---|---|
| 5,676,942 | A | 10/1997 | Testa et al. |
| 6,036,949 | A | 3/2000 | Richards et al. |
| 2004/0086534 | A1 | 5/2004 | Soos et al. |
| 2007/0237723 | A1* | 10/2007 | Cummins ............ A61K 9/0043 424/45 |
| 2009/0155211 | A1 | 6/2009 | Wood et al. |
| 2015/0132261 | A1 | 5/2015 | Cummins et al. |

FOREIGN PATENT DOCUMENTS

| | | |
|---|---|---|
| CN | 101244263 A | 8/2008 |
| WO | 01/23006 | 4/2001 |
| WO | 2008/021536 | 2/2008 |

OTHER PUBLICATIONS

Rajan et al, 2001, Treatment of Hepatitis C related thrombocytopenia with interferon alpha, Amer Jour of Hematology, 68: 202-209.
Farkkila et al, 2013, Neurotoxic and other side effects of high-dose interferon in amyotrophic lateral sclerosis, Acta Neurologica Scandinavica, 70: 42-46.
Proctor et al, 1989, Improvement of platelet counts in steroid-unreponsive idiopathic immune throbocytopenia purpura after short-course therapy wiht recombinant alpha 2b interferon, Blood, 74(6): 1894-1897.
Ohkoshi et al, 2010, Very-Low-Dose Pegylated Intrerferon α2a Plus Ribavirin Therapy for Advanced Liver Cirrhosis Type C: A Possible Therapeutic Alternative without Splenic Intervention, Case Reports in Gastroenterology, 4: 261-266.
International Serach Report and Written Opinion for PCT/US2013/038785, mailed on Sep. 16, 2013.
國際動物醫藥短波 Yungshin Pharm Ind. Co. Ltd., Aug. 2009, http://www.ysp.com.tw/ysp/Product-Medicine-01.aspx?tc=6b&volumn=200908&sn=8 (English translation provided).
Search Report for Taiwanese Patent Application No. 102115953, completed on May 4, 2016 (English translation provided as attached).
試驗計畫名稱 A Randomized, Double-Blind, Placebo-Controlled Study to Evaluate the Efficacy and Safety of Low-Dose Human Interferon α by the Oral Mucosal Route During the 6-Month Follow-up Period of Standard Combination Therapy for Hepatitis C Virus Infection, http://www1.cde.org.tw/ct_taiwan/search_case2.php. (English translation provided as attached), (2008).

* cited by examiner

*Primary Examiner* — Christine J Saoud
*Assistant Examiner* — Jegathessan Seharaseyon
(74) *Attorney, Agent, or Firm* — Barnes & Thornburg LLP (57) ABSTRACT

An interferon composition is provided for enhancing the platelet count, reducing the recurrence rate of hepatitis, and/or improving the social function of hepatitis patients. The method comprises administering a low dose of IFN (about 5 IU to about 2500 IU of IFN-alpha) to a patient in need thereof. In one embodiment the IFN is alpha IFN or beta IFN, and more particularly, in one embodiment the administered biologically active IFN is human alpha IFN.

9 Claims, 11 Drawing Sheets

FIG. 1

Statistical table (1) of the hepatitis recurrence rate in the participants

| | low-dose group | high-dose group | placebo group |
|---|---|---|---|
| number of participants | | | |
| recurrence | 2 (22.2%) | 3 (30.0%) | 2 (20.0%) |
| non-recurrence | 7 (77.8%) | 7 (70.0%) | 8 (80.0%) |
| P-value | 1.0000$^F$ | 1.0000$^F$ | - |

*The participants of statistical table (1) are chosen from the patients suffering Class-A liver fibrosis.

*Class-A liver fibrosis: FibroIndex ≤1.38

*The P-values in the statistical table (1) are determined by *Fisher's exact test*

FIG. 2

Statistical table (2) of the hepatitis recurrence rate in the participants

| number of participants | low-dose group | high-dose group | placebo group |
|---|---|---|---|
| recurrence | 12 (8.3%) | 43 (44.4%) | 5 (41.7%) |
| non-recurrence | 117 (91.7%) | 5 (55.6%) | 7 (58.3%) |
| P-value | 0.1550$^F$ | 1.0000$^F$ | - |

*The participants of statistical table (2) are chosen from the patients suffering Class-B liver fibrosis.

*Class-B liver fibrosis: 1.70 > FibroIndex ≤1.38

*The P-values in the statistical table (2) are determined by *Fisher's exact test*

FIG. 3

Statistical table (3) of the hepatitis recurrence rate in the participants

| Number of participants | low-dose group | high-dose group | placebo group |
|---|---|---|---|
| recurrence | 8 (40.0%) | 4 (26.7%) | 6 (30.0%) |
| non-recurrence | 12 (60.0%) | 11 (73.3%) | 14 (70.0%) |
| P-value | 0.5073$^F$ | 1.0000$^F$ | - |

*The participants of statistical table (3) are chosen from the patients suffering Class-C liver fibrosis.

*Class-C liver fibrosis: 2.0 < FibroIndex ≥1.70

*The P-values in the statistical table (3) are determined by *Fisher's exact test*

FIG. 4

Statistical table (4) of the hepatitis recurrence rate in the participants

| number of participants | low-dose group | high-dose group | placebo group |
|---|---|---|---|
| recurrence | 7 (38.9%) | 9 (47.4%) | 7 (46.7%) |
| non-recurrence | 11 (61.1%) | 10 (52.6%) | 8 (53.3%) |
| P-value | 0.6526[c] | 0.9675[c] | - |

*The participants of statistical table (4) are chosen from the patients suffering Class-D liver fibrosis.

*Class-D liver fibrosis: FibroIndex ≥2.0

*The P-values in the statistical table (4) are determined by *Fisher's exact test*

FIG. 5 platelet count (PLT) normalization of the participants at week 4

| group | n total | n low PLT | percentage low PLT | n normal PLT | percentage normal PLT | P-value |
|---|---|---|---|---|---|---|
| placebo | 35 | 23 | 65.7% | 12 | 34.3% | -- |
| low-dose | 28 | 12 | 42.9% | 16 | 57.1% | 0.07c |
| high-dose | 32 | 23 | 71.9% | 9 | 28.1% | 0.59c |

*The P-values in the PLT statistical table (1) are determined by chi-square test and comparing the low-dose group and the high-dose group

*The PLT counts are measured in 4th week

FIG. 6 platelet count (PLT) normalization of the participants at week 12

| group | n total | n low PLT | percentage low PLT | n normal PLT | percentage normal PLT | P-value |
|---|---|---|---|---|---|---|
| placebo | 34 | 24 | 70.6% | 10 | 29.4% | -- |
| low-dose | 26 | 13 | 50.5% | 13 | 50.0% | 0.10c |
| high-dose | 27 | 20 | 74.1% | 7 | 25.9% | 0.76c |

*The P-values in the PLT statistical table (2) are determined by chi-square test and comparing the low-dose group and the high-dose group

*The PLT counts are measured in 12th week

FIG. 7 platelet count (PLT) normalization of the participants at week 24

| group | n total | n low PLT | percentage low PLT | n normal PLT | percentage normal PLT | P-value |
|---|---|---|---|---|---|---|
| placebo | 32 | 17 | 53.1% | 15 | 46.9% | - |
| low-dose | 23 | 8 | 34.8% | 15 | 65.2% | 0.18[c] |
| high-dose | 26 | 14 | 53.8% | 12 | 46.2% | 0.96[c] |

*The P-values in the PLT statistical table (3) are determined by *chi-square test* and comparing the low-dose group and the high-dose group

*The PLT counts are measured in 24th week

FIG. 8 platelet count (PLT) normalization of the participants at week 36

| group | n total | n low PLT | percentage low PLT | n normal PLT | percentage normal PLT | P-value |
|---|---|---|---|---|---|---|
| placebo | 32 | 19 | 59.4% | 13 | 40.6% | - |
| low-dose | 22 | 4 | 18.2% | 18 | 81.6% | 0.03[c] |
| high-dose | 24 | 11 | 45.8% | 13 | 54.2% | 0.31[c] |

*The P-values in the PLT statistical table (4) are determined by *chi-square test* and comparing the low-dose group and the high-dose group

*The PLT counts are measured in 36th week

FIG. 9

| group | n total | n low PLT | percentage low PLT | n normal PLT | percentage normal PLT | P-value |
|---|---|---|---|---|---|---|
| placebo | 31 | 18 | 58.1% | 13 | 41.9% | - |
| low-dose | 21 | 4 | 19.0% | 17 | 81.0% | 0.005c |
| high-dose | 24 | 12 | 50.0% | 12 | 50.0% | 0.55c | platelet count (PLT) normalization of the participants at week 48

*The P-values in the PLT statistical table (5) are determined by *chi-square test*
and comparing the low-dose group and the high-dose group

*The PLT counts are measured in 48th week

FIG. 10

Comparison of mean changes in SF-36 questionnaire quality-of-life scores in the participants

| items | low-dose group | high-dose group | placebo group | P-value[I] | P-value[II] |
|---|---|---|---|---|---|
| physical function (PF) | 10.7±18.8 | 16.3±20.1 | 11.0±15.7 | 0.6785[w] | 0.5297[w] |
| role physical (RP) | 39.6±41.8 | 42.9±44.8 | 44.4±42.9 | 0.6313[w] | 0.9520[w] |
| bodily pain (BP) | 19.8±24.5 | 13.9±22.8 | 15.6±23.1 | 0.3893[T] | 0.7385[T] |
| general health (GH) | 5.8±18.3 | 10.6±16.7 | 5.7±18.9 | 0.8745[w] | 0.1219[w] |
| vitality (VT) | 13.5±22.9 | 15.9±20.1 | 13.4±18.9 | 0.8289[w] | 0.5524[w] |
| *social function (SF)* | *21.4±17.9* | *17.0±20.1* | *9.7±21.3* | *0.0030[w]* | *0.0801[w]* |
| role emotional (RE) | 34.0±50.3 | 38.5±41.6 | 28.1±47.6 | 0.5156[w] | 0.2677[w] |
| mental health (MH) | 8.3±17.8 | 3.2±14.3 | 4.2±14.4 | 0.2304[T] | 0.7478 |

TREATMENT OF THROMBOCYTOPENIA USING ORALLY ADMINISTERED INTERFERON

CROSS REFERENCE TO RELATED APPLICATIONS

This application is a continuation application of U.S. Nonprovisional patent application Ser. No. 14/398,647, filed on Nov. 3, 2014, which is a U.S. National Stage Entry Application under 35 U.S.C. §371(b) of International Patent Application No. PCT/US2013/038785, filed Apr. 30, 2013, which claims priority to U.S. Provisional Patent Application No. 61/642,208, filed on May 3, 2012, the disclosures of all of which are hereby expressly incorporated by reference in their entireties.

BACKGROUND

Platelets, also referred to as thrombocytes, are anuclear cell fragments that exist in mammalian blood and mediate blood clot formation and hemostasis. In addition, platelets release growth factors that play a significant role in the repair and regeneration of connective tissues and facilitate wound healing. Platelets are the terminal differentiation product of megakaryocytes (MK), which in turn originate from pluripotent stem cells of the bone marrow. Platelets have an average lifespan of about 5 to 10 days, and their physiological blood level in humans is normally 150,000 to 450,000/uL. When a patient's levels of circulating platelets are depleted below the physiological range, this condition is known as thrombocytopenia.

Thrombocytopenia is typically associated with defective formation of hemostatic plugs and bleeding, wherein the risk of bleeding is inversely proportional to the platelet count. Early diagnosis and treatment are important to prevent progression to more serious symptoms, such as cerebral bleeding.

Four factors (1) failed platelet production, (2) abnormal platelet distribution, (3) increased platelet destruction, and (4) increased platelet consumption are known as the mechanism of thrombocytopenia; however, its pathological features and causes vary widely. Decreased platelet counts can be due to decreased production caused by a number of disease processes including, vitamin B12 or folic acid deficiency, leukemia or myelodysplastic syndrome, decreased production of thrombopoietin by the liver in liver failure, sepsis, systemic viral or bacterial infection, Dengue fever (by direct infection of bone marrow megakaryocytes as well as immunological shortened platelet survival). Decreased platelet counts can be due to a hereditary syndrome, including for example, congenital amegakaryocytic thrombocytopenia (CAMT), Thrombocytopenia absent radius syndrome, Fanconi anemia, Bernard-Soulier syndrome, May-Hegglin anomaly, Grey platelet syndrome, Alport syndrome and Wiskott-Aldrich syndrome. In addition decreased platelet counts can be due to increased destruction of platelets as seen with idiopathic thrombocytopenic purpura (ITP), thrombotic thrombocytopenic purpura (TTP), hemolytic-uremic syndrome (HUS), disseminated intravascular coagulation (DIC), paroxysmal nocturnal hemoglobinuria (PNH), antiphospholipid syndrome, systemic lupus erythematosus (SLE), post-transfusion purpura, neonatal alloimmune thrombocytopenia (NAITP), splenic sequestration of platelets due to hypersplenism and HIV-associated thrombocytopenia. Medications can also produce thrombocytopenia as a negative side effect, including for example the administration of valproic acid, methotrexate, carboplatin, interferon, isotretinoin, panobinostat, and other chemotherapy drugs, Singulair (montelukast sodium) and H2 blockers and proton-pump inhibitors.

In particular, intravenous administration of interferon (IFN) has long been recognized as a therapeutic agent that helps reduce viremia in chronic hepatitis C. Employed widely, it is known that the number of platelets gradually decreases with time after IFNs administration in most patients. IFN must be thus decreased in dose or discontinued in some patients even when continuation of the therapy is desired. The decrease in platelet count is therefore a clinically significant problem. When IFN is administered to patients with hepatic cirrhosis, close attention must be paid, since these patients often exhibit a low platelet count of ≤100,000/uL even before the start of administration. No effective therapeutic method has been established for the adverse drug reaction to IFN.

"Interferon" is a term generically describing a distinct group of cytokines exhibiting pleiotropic activity generally categorized as antiviral, antiproliferative and immunomodulatory. In the early years of IFN research, an international committee was assembled to devise a system for orderly nomenclature of IFNs and defined "interferon" as follows: "To qualify as an interferon a factor must be a protein which exerts virus non-specific, antiviral activity at least in homologous cells through cellular metabolic process involving synthesis of both RNA and protein." Journal of Interferon Research, 1, pp. vi (1980). "Interferon" as used herein in describing the present invention shall be deemed to have that definition and shall contemplate such proteins and glycoproteins, including for example, the subtypes IFN-α, IFN-β, IFN-δ, IFN-γ, IFN-ε, IFN-κ, IFN-λ, IFN-ω and IFN-tau, regardless of their source or method of preparation or isolation.

Originally identified for their ability to induce cellular resistance to viral infection, IFNs are currently known to be potent mediators in the host defense mechanism and homeostasis, modulating both the innate and adaptive immune responses. IFNs are small, inducible 20-25 K, usually glycosylated proteins that are produced by vertebrate cells in response to various biological stimuli. Mechanistically, IFNs mediate their biological activities by binding to receptors present on the surface of target cells. Specific ligand-receptor interactions trigger intracellular signaling cascade downstream, resulting in the synthesis of proteins that mediate mentioned pleiotropic activities.

IFNs are classified into three groups: type I, type II or type III, based on their structure, physicochemical properties and biological activities. In mammals, eight families of type I IFN have been described. These are: IFN-α, IFN-β, IFN-δ, IFN-ε, IFN-κ, IFN-ω and IFN-tau (IFN-τ). Among these families, trophoblast IFN-τ, found only in ruminant ungulates, is not inducible by virus and is produced in the embryonic trophoectoderm at a specific time, early during pregnancy. Its major function is to create conditions for the completion of pregnancy. IFN-δ (delta), a polypeptide of about 149 amino acids, has been described only in pigs; this IFN is physiologically expressed by trophoblasts during the period of implantation in uterus.

IFN-γ is the sole representative of type II IFN in mammals, while IFN-λ is the sole representative of type III IFN in mammals.

Type I, type II and type III IFNs exert their biological effects through different cellular receptors.

As described herein a method for treating or preventing thrombocytopenia in a subject in need thereof, comprising administering to the subject an oral low dose of IFN so as to elevate the levels of platelets in said subject, thereby treating or preventing thrombocytopenia in said subject. More particularly, the method comprises administering IFN for contact with the mucosal membranes of the digestive and respiratory tract.

SUMMARY

A method of treating thrombocytopenia in an individual is provided. More particularly, a method for elevating blood levels of platelets to a concentration of about 150,000 to 450,000 uL in an individual is provided by administering low dose IFN to the individual. In one embodiment the method comprises treating thrombocytopenia that is associated with intravenous IFN therapy. In one embodiment the IFN is either IFN-alpha or IFN beta and the IFN is administered orally, intranasally or by inhalation. In one embodiment the IFN is IFN-alpha and the IFN is administered orally or topically by inhalation in a single daily dosage amount from about 0.1 international units (IU)/lb to about 100 IU/lb of patient body weight. In one embodiment the patient is administered a single daily dosage for 500 IU of IFN until platelet counts reach normal levels. When the IFN is administered by inhalation, a metered dose inhaler can be used that provides a dose from about 75 IU to about 1000 IU of IFN.

In a further embodiment an interferon composition is provided for enhancing the platelet count, reducing the recurrence rate of hepatitis, and/or improving the social function of hepatitis patients, wherein the composition comprises two interferons. In one embodiment the two interferons are both type I interferons, IFN-α2b and IFN-α8a, respectively. The relative percentage of the first to the second interferon in the compositions can vary from 5% to 95%, and the percentage of the second interferon to the first can range from 95% to 5%. In one embodiment, the first and second interferons are type I interferons of IFN-α, produced by gene recombinant engineering or through a virus-induced-leukocytosis method. In one embodiment of the present disclosure, the dosage of the interferon composition taken by an adult ranges between 5 IU per day and 1,000 IU per day.

DETAILED DESCRIPTION

Definitions

In describing and claiming the invention, the following terminology will be used in accordance with the definitions set forth below.

As used herein, the term "treating" includes prophylaxis of the specific disorder or condition, or alleviation of the symptoms associated with a specific disorder or condition and/or preventing or eliminating said symptoms.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents and includes agents approved by a regulatory agency of the US Federal government or listed in the US Pharmacopeia for use in animals, including humans. The term "carrier" refers to a diluent, adjuvant, excipient or vehicle with which an active agent is administered.

As used herein term "thrombocytopenia" is a condition in which an individual's blood has less than 150,000 platelets per microliter.

EMBODIMENTS

A method is provided herein for elevating peripheral blood levels of platelets to a concentration of about 150,000 to 450,000 uL in an individual suffering from thrombocytopenia. The method comprises administering a low dose of IFN to a patient in need thereof. In one embodiment the IFN is alpha IFN or beta IFN, and more particularly, in one embodiment the administered biologically active IFN is human alpha IFN.

In a further embodiment, compositions comprising IFN are administered to patients for reducing the recurrence rate of hepatitis, and/or improving social function of hepatitis patients, optionally in combination with treatment with Ribavirin.

In one embodiment an interferon composition is provided for enhancing the platelet count, reducing the recurrence rate of hepatitis, and/or improving the social function of hepatitis patients, wherein the composition comprises two interferons. In one embodiment the composition comprises a first interferon and a second interferon wherein both the first and second IFNs are type I interferons of IFN-α, produced by gene recombinant engineering or through a virus-inducedleukocytosis method. In one embodiment, the first interferon and the second interferon are the type I interferons IFN-α2b and IFN-α8a, respectively. In this interferon composition, the percentage of the first interferon ranges from 5% to 95%, and the percentage of the second interferon ranges from 95% to 5%. In one embodiment, the interferon composition is formulated into a lozenge by use of an excipient, and the ratio of the first interferon to the second interferon in the final interferon composition is 3:1. Of course, excepting the lozenge, the interferon composition of the present invention can be further formulated into any other solid forms or liquid forms after being mixed with different medical additives, such an adjuvant, a diluent, or a carrier.

The IFN can be administered to the patient to treat thrombocytopenia through a number of routes, including orally, intranasally, by inhalation or via a nebulizer. In accordance with one embodiment the IFN is administered orally. The IFN containing composition can be administered in a single dose, or in several doses per day. In one embodiment the orally administered IFN is administered in doses of 5, 10, 15, 25, 50, 100, 100, 250, 500, or 750 IU, wherein the total daily dosage ranges from 5 to 1500, 25 to 1000 or 150 to 600 IU. In one embodiment, the method comprises the step of administering IFN buccally, sublingually, or by oral ingestion at a dose of about 1 to about 1500 IU of IFN per day. In one embodiment the IFN containing composition is administered once daily at a dosage of 100, 200, 300, 400, 500, 600, 700, 800, 900, 1000 IU. In one embodiment the IFN containing composition is administered once daily at a dosage ranging from 200 to 600 IU. In one embodiment the IFN containing composition is administered once daily at a dosage of about 500 IU.

In a further embodiment the administered IFN is a Type I IFN, formulated in a pharmaceutically acceptable solid dosage form or a pharmaceutically acceptable liquid dosage form. In one embodiment the solid dosage form is a saliva-soluble solid dosage form of IFN-alpha, such as orally dissolving lozenge, which is introduced into the mouth of the patient and held in the mouth for a period of time sufficient to dissolve in saliva in the patient's mouth to form an IFN-containing solution.

IFN of human and murine origin is quantified in the art in terms of International Units (IU). IFNs of other than human or murine origin can be used in accordance with this invention. In that presently accepted practices may not extend the use of "International Units" to quantify non-human and non-murine IFNs, it shall be understood that administration of amounts of non-human/non-murine IFNs having the same efficacy as the quantities (IU's) of human IFN specified in this description are within the scope of the present invention.

In one embodiment the IFN is a type II IFN that is administered orally in a low dosage form, and in one embodiment the IFN is IFN-gamma. In one embodiment, wherein the IFN containing composition is administered orally, the composition is administered in a form or manner that optimizes contact of the composition with the oral and oral pharyngeal mucosa of the animal or human. In one embodiment the IFN containing composition is prepared as a lozenge, powder, liquid or chewable composition.

For the purpose of the present invention, low dosage IFN-alpha treatment dosages range from about 0.1 IU/lb to about 100 IU/lb of patient body weight, more typically about 0.5 to about 10 IU/lb of patient body weight. Thus, unit dosage forms for human use typically comprise about 5 IU to about 2500 IU of IFN-alpha, more typically about 10 IU to about 500 IU of IFN-alpha, in combination with a pharmaceutically acceptable carrier therefor. Dosage forms for treatment in accordance with this invention can be in solid, liquid, aerosol, ointment or cream formulation and are typically administered from one to four times daily until the condition being treated is alleviated. In one embodiment, human IFN-alpha is orally administered in a sterile aqueous solution. Chronic administration may be required for sustained benefit. Generally speaking, the dosage forms are administered in a disease state-dependent manner, including particularly administration topically, bucally/sublingually, by oral ingestion or by inhalation.

In one embodiment a method is provided for treating patients suffering from thrombocytopenia. The method comprises orally administering a low dose of IFN to said patient. In one embodiment the administered IFN is IFN-alpha, administered in an amount effective to enhance peripheral blood platelet counts. In one embodiment the IFN is administered orally, as a solution, or bucally, using a dissolving lozenge or other slow release formulation, or by inhalation, using a spray or mist. In one embodiment the oral IFN is delivered via a solid oral dose formulation, a "lozenge", to allow the patient to suck on the tablet rather than chewing or swallowing it. This allows the IFN in the lozenge to be released slowly and attach to receptors in the oral cavity. In one embodiment the orally administered IFN is IFN-alpha administered in a daily dosage of 400-600 IU or about 500 IU.

In one embodiment a method of treating a human patient suffering from thrombocytopenia induced by intravenous IFN treatment is provided wherein the method speeds the return to normal blood levels of platelets after termination of the intravenous IFN treatment. In one embodiment the method comprises the steps of orally administering IFN in a daily dosage of 1 to 1500 IU. In one embodiment the daily dosage is about 300 to 700 IU, about 400 to 600 IU or about 500 IU. In one embodiment the IFN is IFN-alpha formulated in a liquid or saliva-soluble lozenge dosage form. The method comprises the steps of introducing the liquid or saliva-soluble lozenge dosage form into the mouth of the patient, allowing the dosage form to dissolve in the patient's mouth (where necessary) to form an IFN-containing solution, and contacting the IFN-containing solution with the patient's oral and pharyngeal mucosa to stimulate a therapeutic effect.

In one embodiment the orally administered low dosage IFN is administered immediately after completion of the intravenous IFN treatment. Typically the orally administered IFN is continued until blood platelet levels return to normal (e.g., at or above 150,000 platelets per microliter). In one embodiment the orally administered IFN treatments are continued for up to an additional two weeks after blood platelet levels return to normal.

Example 1

Treatment of Thrombocytopenia with Orally Administered Interferon Alpha

A total of 169 subjects with a history of hepatitis C virus (HCV) infection, genotype 1b, who were in virologic remission after standard treatment with a combination of high-dose injectable IFN plus oral Ribavirin, were enrolled in a double-blind, Phase 2 clinical trial. Immediately after completing this standard therapy, subjects were randomly assigned to daily treatment with 500 or 1500 international IU of IFN-alpha, or matching placebo given via orally dissolving lozenges. Treatment was administered for 24 weeks, followed by 24 weeks of untreated observation. Subjects were assessed for platelet (PLT) count at screening and at study weeks 4, 12, 24, 36 and 48.

Of the 169 randomized subjects, 11 subjects dropped out after only 1-2 weeks of treatment, including 2 subjects who did not meet all eligibility criteria. A total of 158 subjects completed at least 4 weeks of treatment and were therefore evaluable for change in PLT count. Among these 158 evaluable subjects, the proportion of males and females did not differ across the three treatment groups, and the groups did not differ significantly in age or length of prior IFN therapy.

In addition to the 11 subjects who were excluded from analysis because they were unevaluable for changes in PLT count, 26 subjects who completed the week 4 study visit dropped out prior to week 48. While all 26 of these partially evaluable drop-outs had follow-up blood work after leaving the study, only those subjects who remained active at a particular study visit were included in the analysis of PLT count for that visit. There were no significant differences between the groups with respect to the proportion of subjects who dropped out after week 4 for a particular reason or overall.

Analysis of Platelet Count

At each visit, the three treatment groups were compared by analysis of variance (ANOVA) for mean PLT count and mean change in PLT count. When ANOVA detected a significant difference among the three groups, the groups were then individually compared to each other by two-sample T-test. Results of these analyses are discussed below.

The groups did not differ significantly in mean PLT count at screening, but ANOVA showed borderline significant differences (P<0.10) between the groups at weeks 4 and 12, and significant differences (P<0.05) at weeks 24, 36 and 48 (Table 1). Individual comparisons showed that the 500 IU group had a significantly greater mean PLT count at all visits after baseline, compared to placebo (Table 1). The 1500 IU group did not differ from the placebo group at any visit with respect to mean PLT count.

At all visits, absolute changes in PLT count were numerically greatest in the 500 IU group when all evaluable subjects were considered, but the differences among the groups did not reach statistical significance as assessed by ANOVA (data not shown). Significant differences were noted when the 158 evaluable subjects were divided into two groups based on baseline PLT count. Regardless of treatment group, those subjects (n=95) with a baseline PLT count below the normal range (i.e. <150,000) had significantly greater mean increases in PLT count at all visits compared to subjects (n=63) with a PLT count that was in the normal range (data not shown).

Within the 95 subjects with low PLT count at screening, ANOVA applied to mean changes in PLT count revealed borderline significant differences at weeks 4 and 12 and significant differences at weeks 24, 36 and 48 between the three treatment groups. Two-way group comparisons found a significantly greater mean increase in PLT count in the 500 IU group, compared to placebo at all visits other than week 36 (Table 2). There were no significant differences between the placebo and 1500 IU groups.

Within the 63 subjects with a PLT count within the normal range at screening, ANOVA applied to mean changes in PLT count across the three treatment groups found no significant differences at any study visit (data not shown).

Normalization of Platelet Count

For this analysis, the 158 evaluable subjects were split into two categories based on PLT count at screening: "low PLT"=PLT count<150,000 and "normal PLT"=PLT count≥150,000. Chi-square analysis was applied to the proportion of subjects in each group in each of the two categories of PLT counts. The result was non-significant at baseline, indicating no differences between the groups at the start of the study, but was significant (weeks 4, 12, 36 and 48) or borderline significant (week 24) at all other visits (data not shown), indicating differences among the groups.

Consequently, 2×2 chi-square comparisons between the groups were carried out. At each visit, the number of subjects who improved from a low PLT count at baseline to a normal PLT count was compared between the groups. A borderline significantly greater proportion of subjects in the 500 IU group improved from low to normal PLT count at weeks 4 and 12, compared to the placebo group, and a similar trend was noted at week 24 (Tables 3-5). By weeks 36 and 48, significantly more subjects in the 500 IU group had experienced normalization of PLT count, compared to the placebo group (Tables 6-7). There were no differences between the 1500 IU and placebo group at any visit in the proportion of subjects exhibiting normalization of PLT count.

Of the 63 subjects in the sub-group who started the study with a PLT count in the normal range, only 4 ended the study with a low PLT count. This included 2 subjects in the placebo group and 1 subject in each of the IFN groups (data not shown).

DISCUSSION

High dose injectable IFN-alpha is known to cause a reduction in PLT count via suppression of the bone marrow. Of 158 evaluable subjects, 95 (60%) had a starting PLT count that was below normal, indicating that PLT counts were suppressed by the injectable IFN the subjects received just prior to entering the study.

The treatment groups did not differ in mean platelet count at baseline, but at all other study visits the subjects who received 500 IU of IFN-alpha once per day had a significantly greater mean PLT count than the placebo group. While changes in mean PLT count did not differ significantly between the groups overall, subjects in the 500 IU group who had a PLT count that was below the normal range at baseline showed significantly greater increases in PLT count than both the placebo and 1500 IU groups.

The groups did not differ at entry in the proportion of subjects with a low PLT count, but by the end of the study nearly twice as many subjects who received daily treatment with oral IFN-alpha at 500 IU per day had normalization of their platelet count, compared to those given placebo.

It is not surprising that PLT counts would rise in the study subjects once they stopped taking injectable IFN, and would rise more in subjects with low baseline counts, but similar improvement would have been expected in all 3 groups. Instead, it appears that treatment with oral IFN at 500 IU once per day helped subjects recover from the thrombocytopenic effects of injectable IFN faster than placebo. Importantly, oral IFN therapy did not cause platelet counts to rise above the normal range but instead improved the platelet counts into the normal range, thereby indicating that oral IFN treatment is safe.

The positive effects of oral IFN observed in this study were seen in the group that was treated with 500 IU once per day but not the group receiving 1500 IU once per day. The group that received treatment with 500 IU three times per day showed no improvement relative to placebo. When delivered into the mouth, IFN-alpha attaches to receptors in the oral mucosa and induces systemic host defense mechanisms without the IFN actually entering the circulation. It is known that overstimulation can lead to internalization of receptors on cell surfaces, which blocks their activity. It may be that in the 1500 IU group, subjects receiving 3 doses taken over a 12-hour period over stimulated their IFN receptors, causing them to internalize and become inactive.

TABLE 1

Mean Platelet Counts in Evaluable Subjects

| Group | n | Mean | Std Dev | P-value* |
|---|---|---|---|---|
| Platelet Count at Screening ||||| 
| placebo | 55 | 133.9 | 50.9 | — |
| 500 IU | 55 | 150.4 | 54.1 | 0.10 |
| 1500 IU | 48 | 138.7 | 71.1 | 0.69 |
| Total | 158 | 141.1 | 58.8 | 0.32** |
| Platelet Count at Week 4 |||||
| placebo | 55 | 158.8 | 53.7 | — |
| 500 IU | 55 | 185.4 | 56.7 | 0.01 |
| 1500 IU | 48 | 165.1 | 69.5 | 0.61 |
| Total | 116 | 170.0 | 59.9 | 0.06** |
| Platelet Count at Week 12 |||||
| placebo | 51 | 151.9 | 51.5 | — |
| 500 IU | 52 | 177.1 | 49.1 | 0.01 |
| 1500 IU | 43 | 160.9 | 67.4 | 0.47 |
| Total | 146 | 163.5 | 55.9 | 0.07** |
| Platelet Count at Week 24 |||||
| placebo | 48 | 162.8 | 58.3 | — |
| 500 IU | 48 | 195.7 | 48.7 | 0.004 |
| 1500 IU | 40 | 165.2 | 59.6 | 0.85 |
| Total | 136 | 175.1 | 55.5 | 0.007** |
| Platelet Count at Week 36 |||||
| placebo | 48 | 163.8 | 56.3 | — |
| 500 IU | 47 | 194.5 | 52.0 | 0.007 |
| 1500 IU | 39 | 171.8 | 60.3 | 0.53 |
| Total | 134 | 176.9 | 56.0 | 0.03** |
| Platelet Count at Week 48 |||||
| placebo | 47 | 167.6 | 59.0 | — |
| 500 IU | 46 | 203.4 | 52.7 | 0.003 |
| 1500 IU | 39 | 167.0 | 53.1 | 0.96 |
| Total | 132 | 179.9 | 55.1 | 0.002** |

*Two-sample t-test comparison to the placebo group.
**One-way analysis of variance between the 3 treatment groups.

TABLE 2

Changes in Platelet Count in Subjects with a Low Platelet Count at Entry

| Group | n | Mean | Std Dev | P-value* |
|---|---|---|---|---|
| Change in Platelet Count at Week 4 |||||
| placebo | 35 | 30.9 | 25.2 | — |
| 500 IU | 28 | 47.2 | 28.5 | 0.02 |
| 1500 IU | 32 | 32.8 | 35.4 | 0.81 |
| Total | 95 | 36.3 | 29.9 | 0.08** |
| Change in Platelet Count at Week 12 |||||
| placebo | 34 | 31.2 | 27.7 | — |
| 500 IU | 26 | 39.8 | 25.2 | 0.32 |
| 1500 IU | 27 | 22.1 | 26.5 | 0.42 |
| Total | 87 | 30.9 | 26.6 | 0.06** |

TABLE 2-continued

Changes in Platelet Count in Subjects with a Low Platelet Count at Entry

| Group | n | Mean | Std Dev | P-value* |
|---|---|---|---|---|
| Change in Platelet Count at Week 24 |||||
| placebo | 32 | 37.5 | 28.3 | — |
| 500 IU | 23 | 59.0 | 33.0 | 0.01 |
| 1500 IU | 26 | 33.3 | 26.8 | 0.57 |
| Total | 81 | 42.3 | 29.2 | 0.006** |
| Change in Platelet Count at Week 36 |||||
| placebo | 32 | 40.2 | 35.3 | — |
| 500 IU | 22 | 58.1 | 25.3 | 0.05 |
| 1500 IU | 24 | 38.3 | 25.4 | 0.82 |
| Total | 78 | 44.7 | 29.9 | 0.05** |
| Change in Platelet Count at Week 48 |||||
| placebo | 31 | 43.0 | 32.8 | — |
| 500 IU | 21 | 72.3 | 31.4 | 0.002 |
| 1500 IU | 24 | 38.4 | 29.1 | 0.59 |
| Total | 76 | 49.6 | 31.3 | 0.0009** |

*Two-sample t-test comparison to the placebo group.
**One-way analysis of variance between the 3 treatment groups.

TABLE 3

Normalization of Platelet Count from Baseline to Week 4

| Group | n | low PLT | % low | normal PLT | % normal | P-value* |
|---|---|---|---|---|---|---|
| placebo | 35 | 23 | 65.7% | 12 | 34.3% | — |
| 500 IU | 28 | 12 | 42.9% | 16 | 57.1% | 0.07 |
| 1500 IU | 32 | 23 | 71.9% | 9 | 28.1% | 0.59 |
| Total | 95 | 58 | 61.1% | 37 | 38.9% | 0.02** |

*Chi-square test comparison to the placebo group.
**Comparison between the IFN groups.

TABLE 4

Normalization of Platelet Count from Baseline to Week 12

| Group | n | low PLT | % low | normal PLT | % normal | P-value* |
|---|---|---|---|---|---|---|
| placebo | 34 | 24 | 70.6% | 10 | 29.4% | — |
| 500 IU | 26 | 13 | 50.0% | 13 | 50.0% | 0.10 |
| 1500 IU | 27 | 20 | 74.1% | 7 | 25.9% | 0.76 |
| Total | 87 | 57 | 65.5% | 30 | 34.5% | 0.07** |

*Chi-square test comparison to the placebo group.
**Comparison between the IFN groups.

TABLE 5

Normalization of Platelet Count from Baseline to Week 24

| Group | n | low | % | normal | % | P-value* |
|---|---|---|---|---|---|---|
| placebo | 32 | 17 | 53.1% | 15 | 46.9% | — |
| 500 IU | 23 | 8 | 34.8% | 15 | 65.2% | 0.18 |
| 1500 IU | 26 | 14 | 53.8% | 12 | 46.2% | 0.96 |
| Total | 81 | 39 | 48.1% | 42 | 51.9% | 0.18** |

*Chi-square test comparison to the placebo group.
**Comparison between the IFN groups.

TABLE 6

Normalization of Platelet Count from Baseline to Week 36

| Group | n | low | % | normal | % | P-value* |
|---|---|---|---|---|---|---|
| placebo | 32 | 19 | 59.4% | 13 | 40.6% | — |
| 500 IU | 22 | 4 | 18.2% | 18 | 81.8% | 0.003 |
| 1500 IU | 24 | 11 | 45.8% | 13 | 54.2% | 0.31 |
| Total | 78 | 34 | 43.6% | 44 | 56.4% | 0.05** |

*Chi-square test comparison to the placebo group.
**Comparison between the IFN groups.

TABLE 7

Normalization of Platelet Count from Baseline to Week 48

| Group | n | low | % | normal | % | P-value* |
|---|---|---|---|---|---|---|
| placebo | 31 | 18 | 58.1% | 13 | 41.9% | — |
| 500 IU | 21 | 4 | 19.0% | 17 | 81.0% | 0.005 |
| 1500 IU | 24 | 12 | 50.0% | 12 | 50.0% | 0.55 |
| Total | 76 | 34 | 44.7% | 42 | 55.3% | 0.03** |

*Chi-square test comparison to the placebo group.
**Comparison between the IFN groups.

Example 2

(A) Participants

The participants were chosen from an adult group older than 21 years of age, wherein the participants were all infected with hepatitis C virus (HCV) of genotype 1b, and had all achieved viral clearance by treatment with pegylated IFN in combination with Ribavirin.

Figure 1:
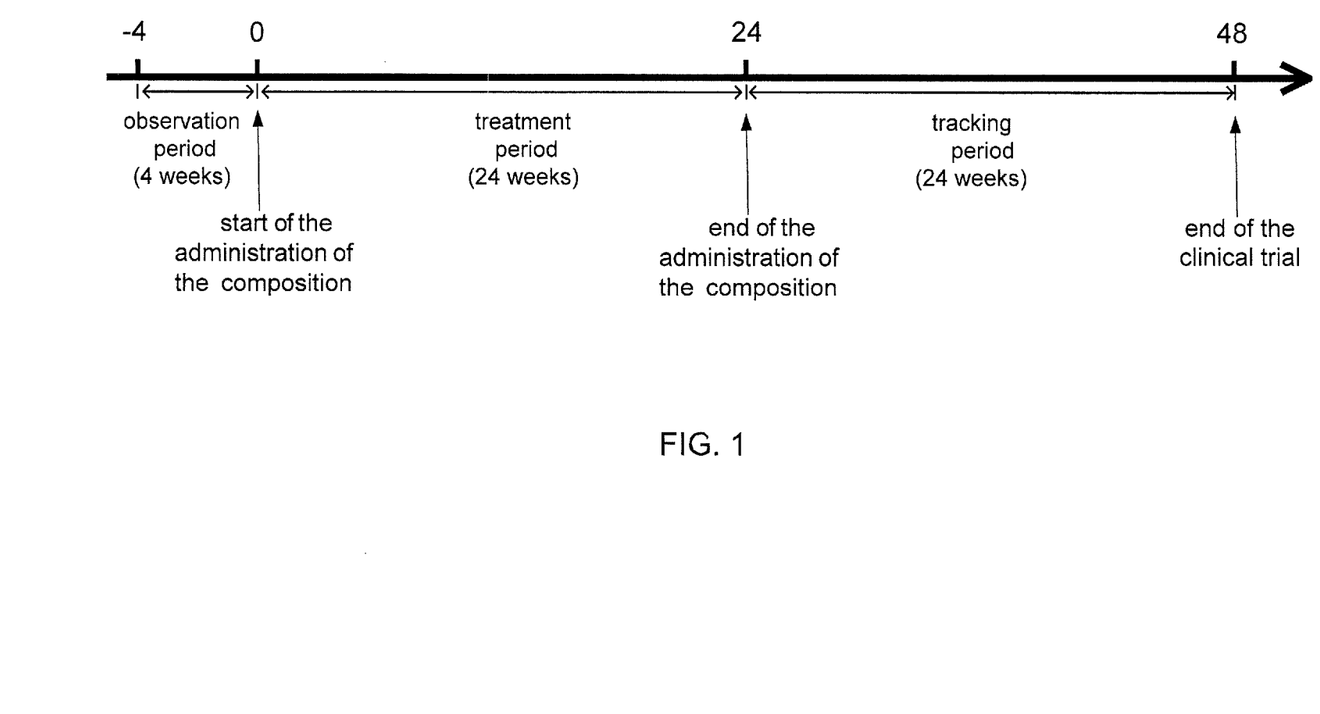
FIG. 1 is provides a time-distance diagram of the clinical trial disclosed in Example 2.
Figure 2:
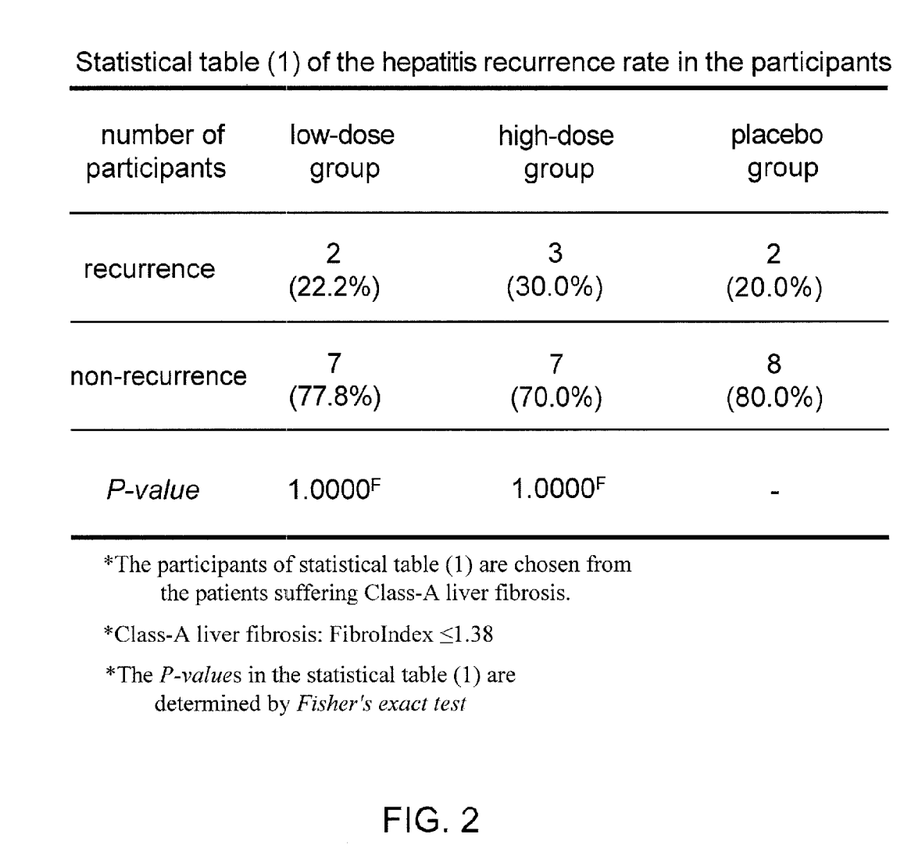
FIG. 2 is a table showing the hepatitis recurrence rate in patients with Class A fibrosis in the clinical study disclosed in Example 2.
Figure 3:
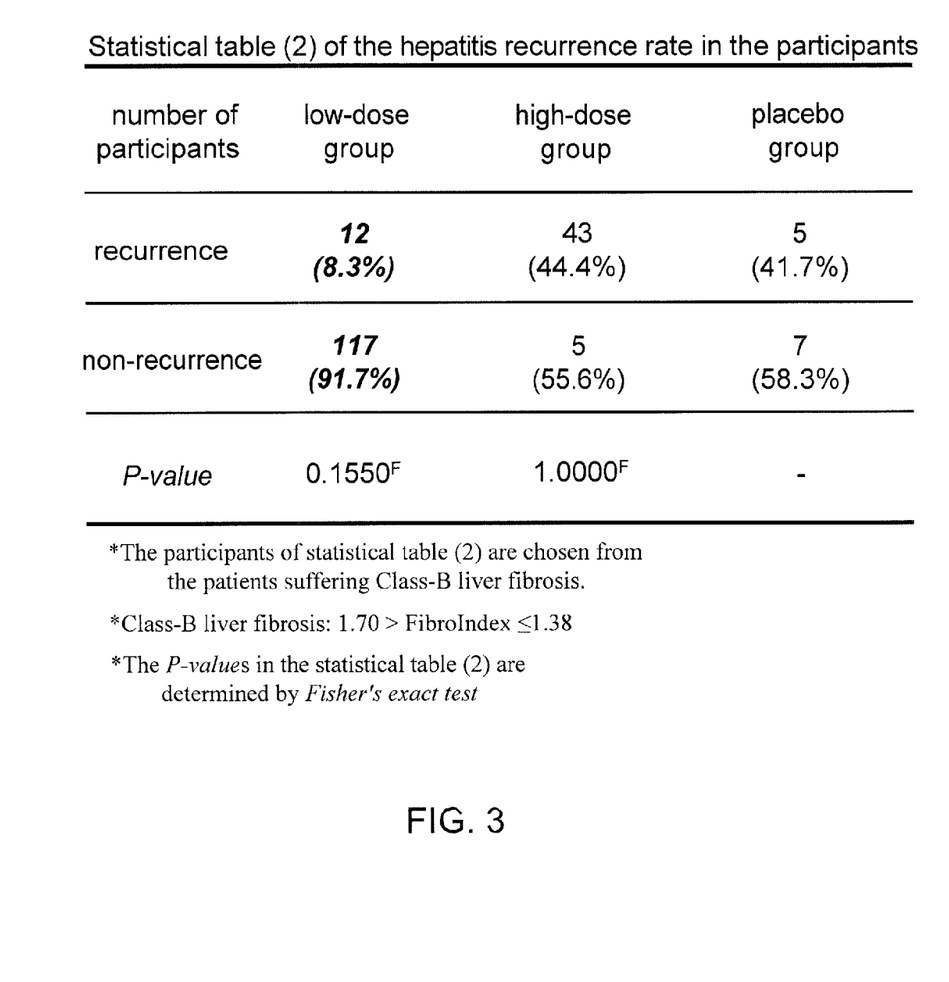
FIG. 3 is a table showing the hepatitis recurrence rate inpatients with Class B fibrosis in the clinical study disclosed in Example 2.
Figure 4:
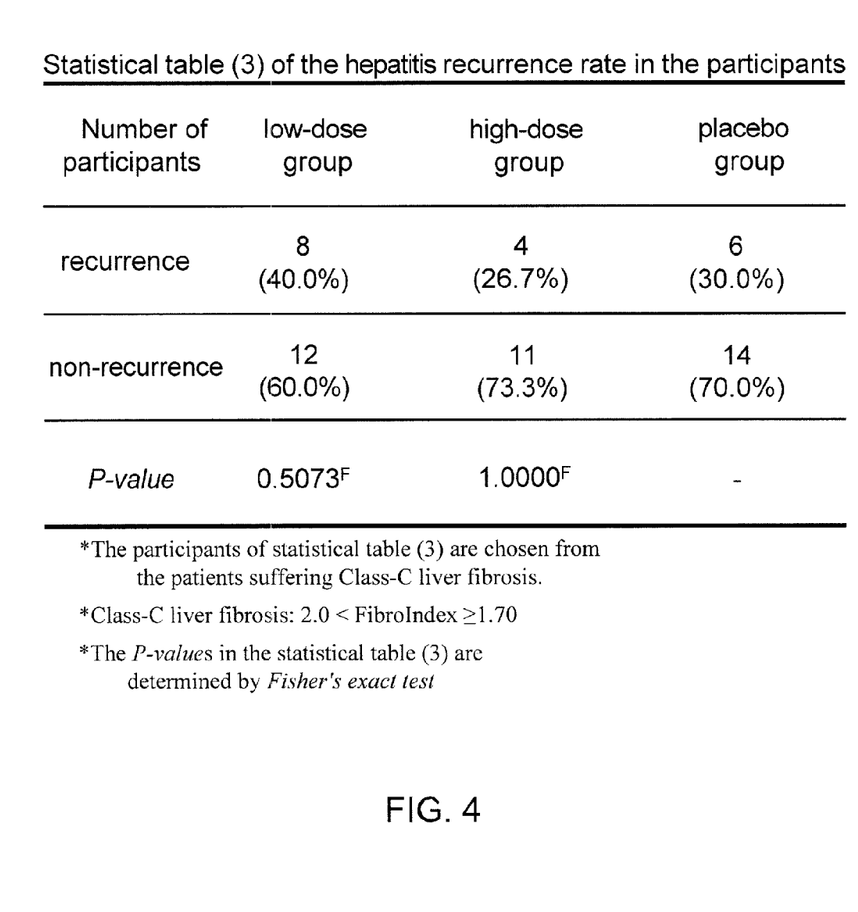
FIG. 4 is a table showing the hepatitis recurrence rate in patients with Class C fibrosis in the clinical study disclosed in Example 2.
Figure 5:
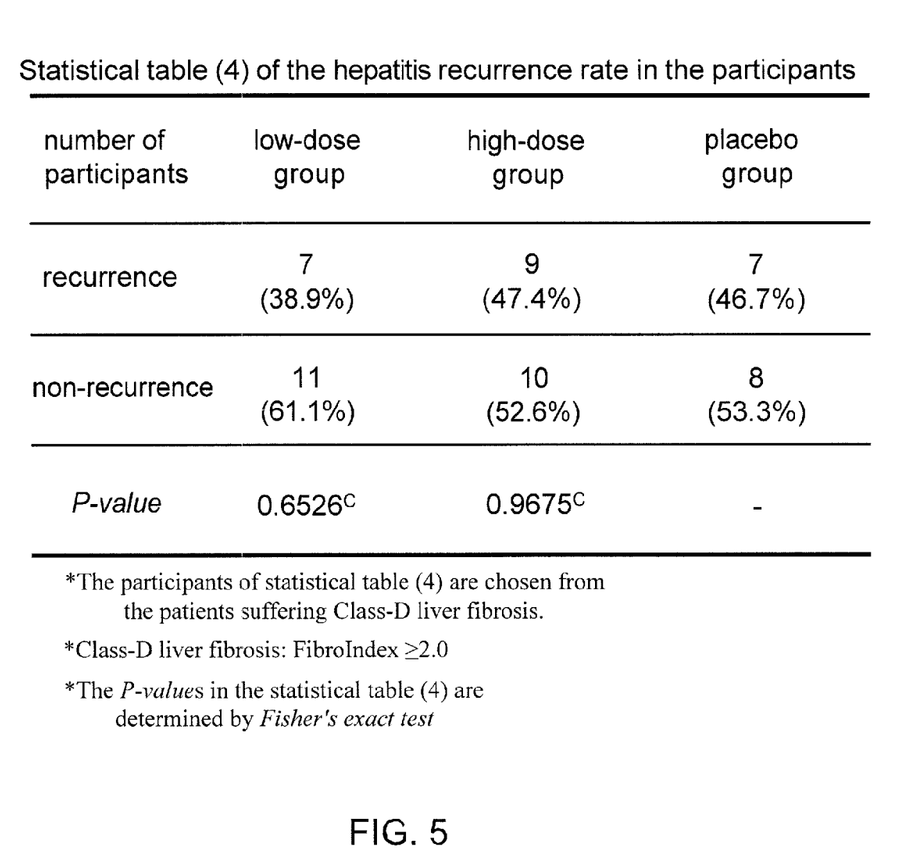
FIG. 5 is a table showing the hepatitis recurrence rate in patients in the clinical study with Class D fibrosis disclosed in Example 2.
Figure 6:
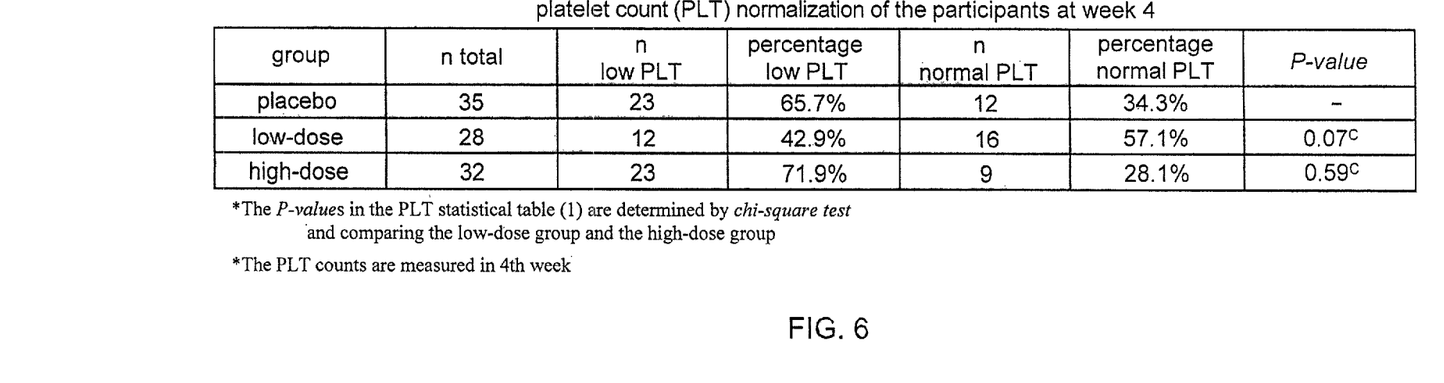
FIG. 6 is a table showing the rate of platelet count normalization in patients at 4 weeks in the clinical study disclosed in Example 2.
Figure 7:
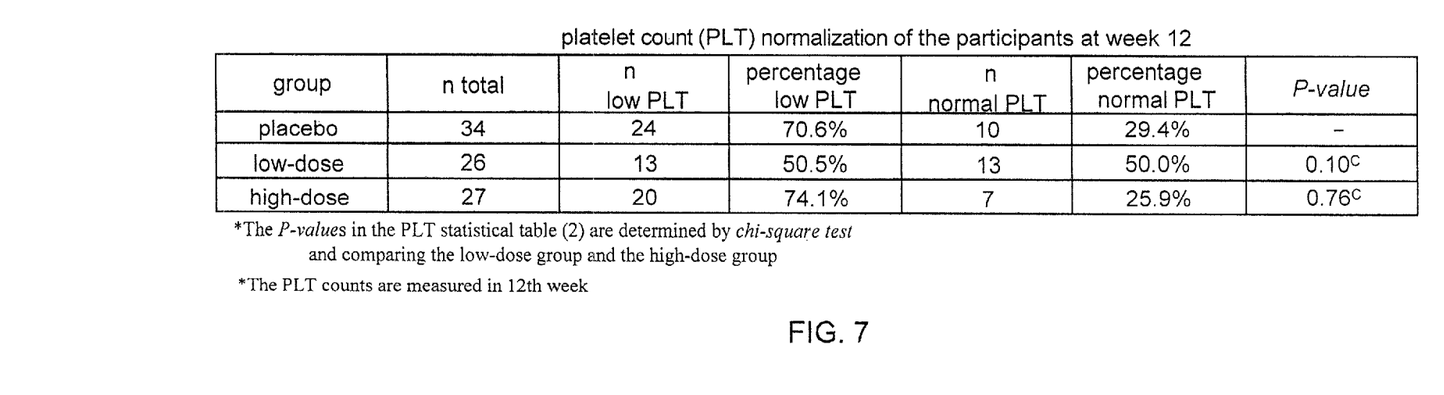
FIG. 7 is a table showing the rate of platelet count normalization at 12 weeks in patients in the clinical study disclosed in Example 2.

(B) Test Flow of the Clinical Trial (See FIG. 1)

(Week −4) All eligible participants were randomized into 3 groups, including 59, 53 and 57 participants in a low-dose group, a high-dose group and a placebo group, respectively.

(Week 0) This point represented the start of administration of the interferon composition of the present invention of 500 IU and 1500 IU to the participants in the low-dose group and the high-dose group, respectively, and the placebo lozenge to the participants in the control group.

(Week 24) This point marked the end of the administration of the interferon composition and the placebo, and the start of an untreated continuous observation (tracking) phase of the participants in the 3 groups for 24 weeks.

(Week 48) The clinical trial ended at the 48th week.
FIGS. 2-5 correspond to statistical table (1), statistical table (2), statistical table (3), and statistical table (4) which show the viral hepatitis recurrence rate of the participants in the 3 groups based on the amount of liver fibrosis observed at baseline. As shown in FIGS. 2-5, in this clinical trial the participants of statistical table (1) are chosen from the patients suffering with class-A liver fibrosis, wherein the class-A liver fibrosis is defined by FibroIndex≤1.38. The participants of statistical table (2) are chosen from the patients suffering with class-B liver fibrosis, and the class-B liver fibrosis is defined by 1.70>FibroIndex≤1.38. The participants of statistical table (3) are chosen from the patients suffering with class-C liver fibrosis, and the class-C liver fibrosis is defined by 2.0<FibroIndex≥1.70. Moreover, the participants of statistical table (4) are chosen from the patients suffering with class-D liver fibrosis, and the class-D liver fibrosis is defined by FibroIndex≥2.0. As shown by the data in FIG. 3, the 500 IU interferon composition is able to reduce the hepatitis recurrence rate of the patients suffering with class-B liver fibrosis to 8.3%, compared to a hepatitis recurrence rate in the placebo patients suffering with class-B liver fibrosis of 41.7%. Thus, the clinical trial results proved that the interferon composition of the present invention is indeed capable of reducing the recurrence rate of hepatitis.

Figure 8:
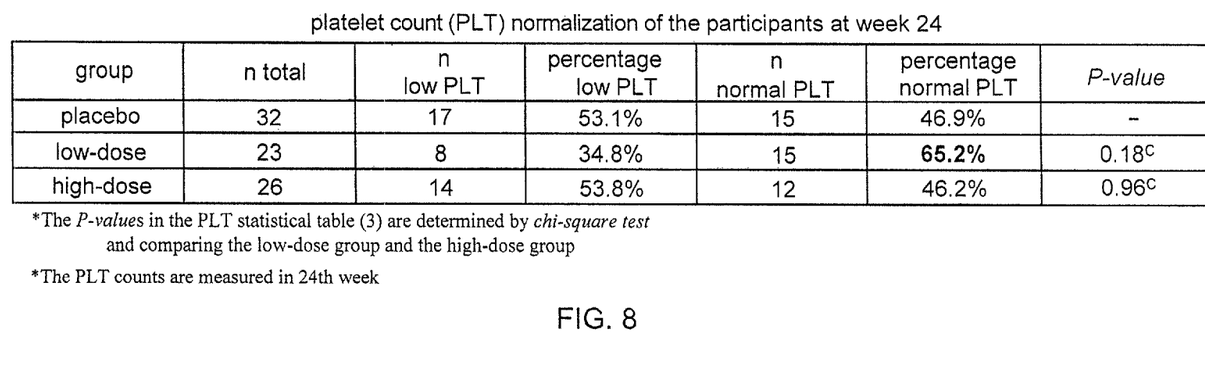
FIG. 8 is a table showing the rate of platelet count normalization at 24 weeks in patients in the clinical study disclosed in Example 2.
Figure 9:
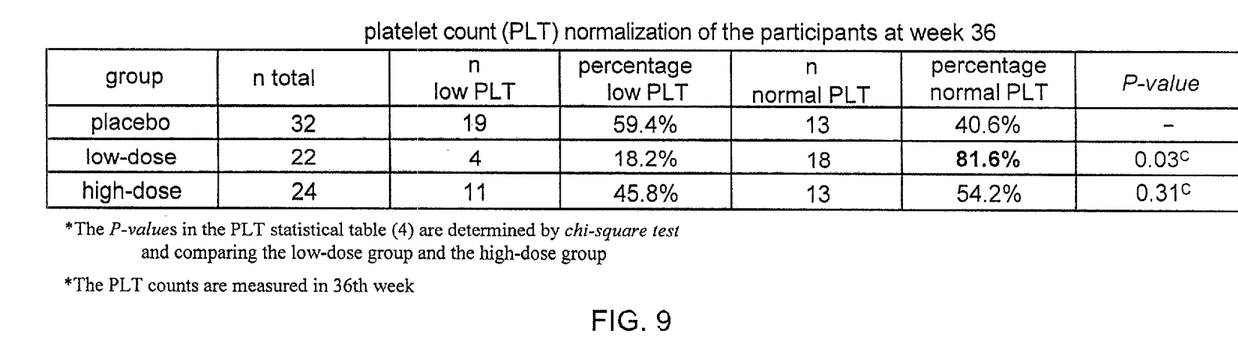
FIG. 9 is a table showing the rate of platelet count normalization at 36 weeks in patients in the clinical study disclosed in Example 2.
Figure 10:
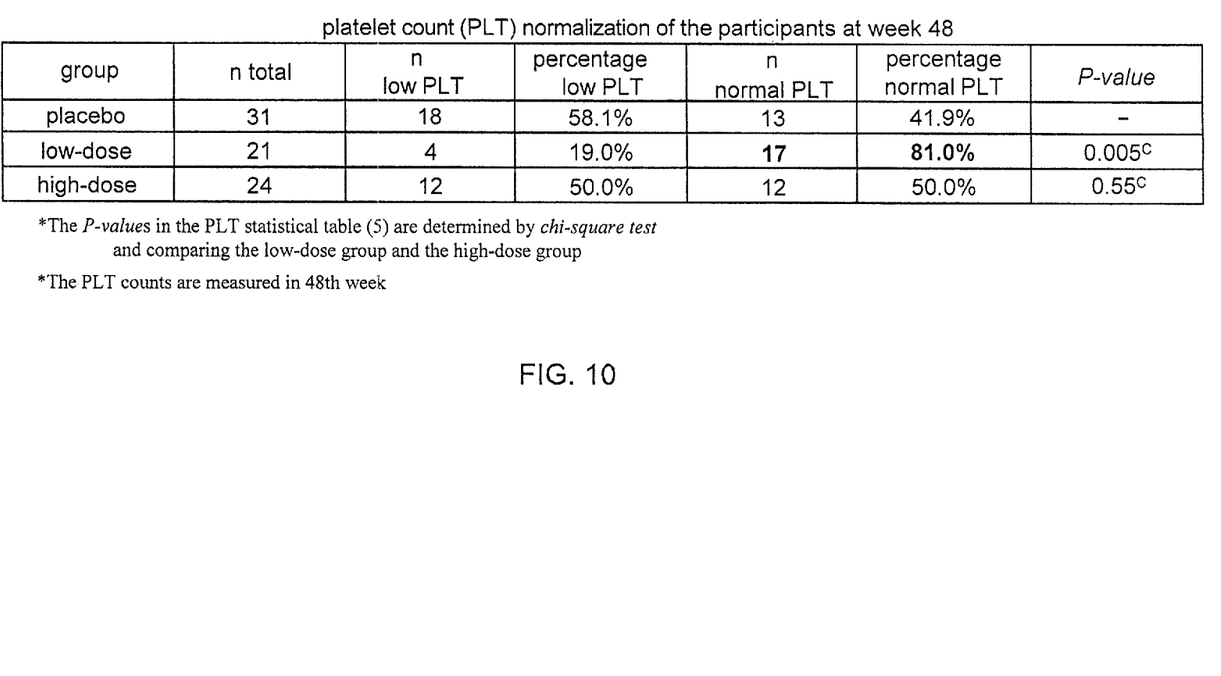
FIG. 10 is a table showing the rate of platelet count normalization at 48 weeks in patients in the clinical study disclosed in Example 2.

FIGS. 6-9 present the rate of platelet (PLT) count normalization of the participants in 3 groups at weeks 4, 12, 24, 36 and 48, respectively. In FIG. 8, the results indicate that the 500 IU interferon composition does effectively increase the normalization of PLT count of the participants in low-dose group at the 24th week. Moreover, as shown in the FIGS. 9 and 10, the percentage of participants having normal PLT count in the 500 IU interferon group reaches 81% at both 24 and 48 weeks, but the percentage of the participants having normal PLT count in the placebo group reaches only half this level Taken together, the PLT statistical tables (1-4), show that the interferon composition of the present invention enhances the platelet count of HCV patients suffering from low platelets.

Figure 11:
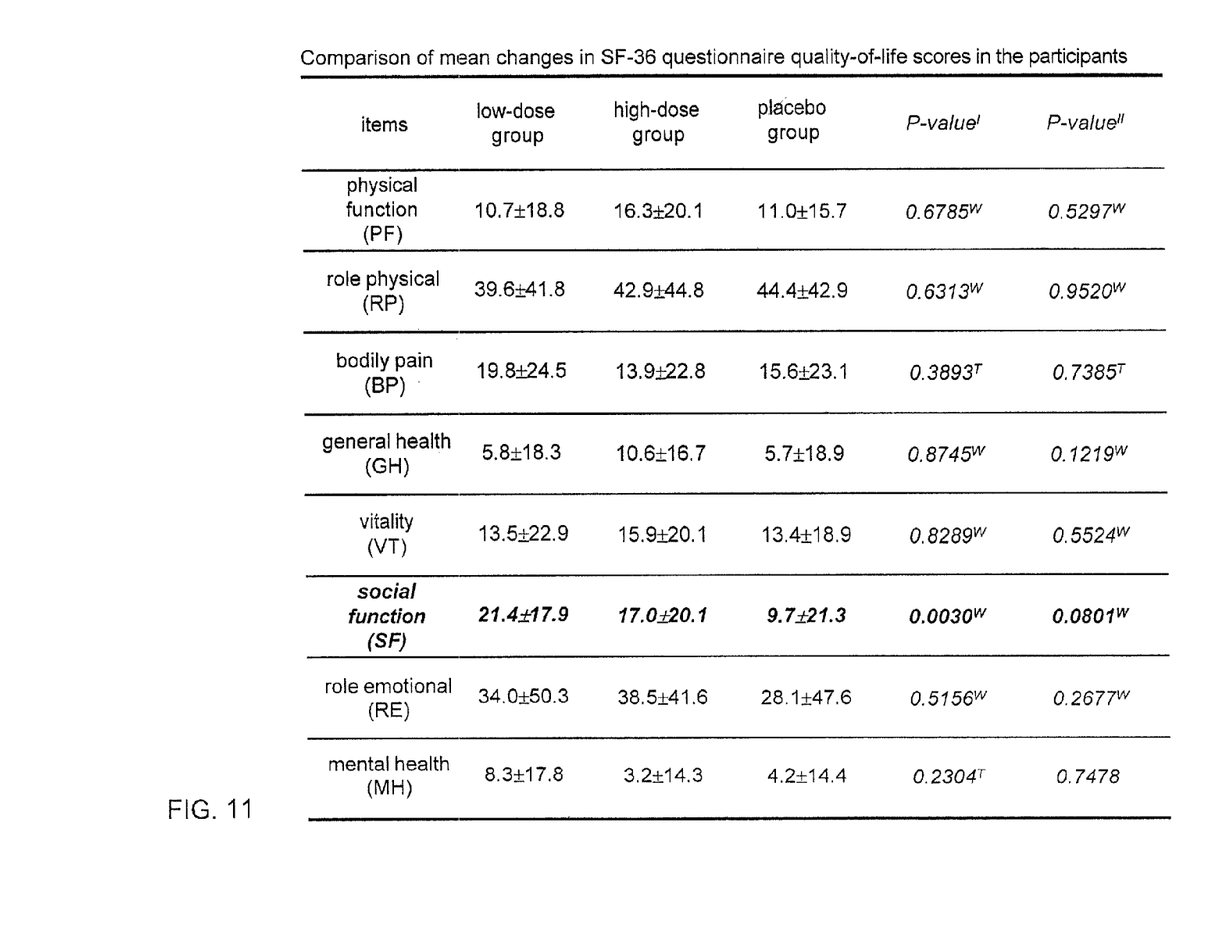
FIG. 11 presents a quality of life statistical table of the participants in the clinical trial disclosed in Example 2.

FIG. 11 illustrates a statistical table of quality of life (QOL) changes of the participants in the 3 groups as assessed by the SF-36 questionnaire. As shown in FIG. 11, the 500 IU interferon composition enhanced the social function (SF) score of the participants by 21 points, while the placebo group had an SF score increase of only 9.7 points. Accordingly, the clinical trial results demonstrate that the interferon composition of the present invention is capable of enhancing the social function (SF) of the patients with hepatitis C. Herein, it needs to be explained that the numeric values of the "P-valueI" in the QOL statistical table are determined by comparing the low-dose group and the placebo group, while the numeric values of the "P-valueII" are determined by comparing the high-dose group and the placebo group. In addition, the P-values marked "W" in the QOL statistical table were determined by the Wilcoxon rank sum test, and the P-values marked "T" were determined by Two-sample T-test.

Figure 12:
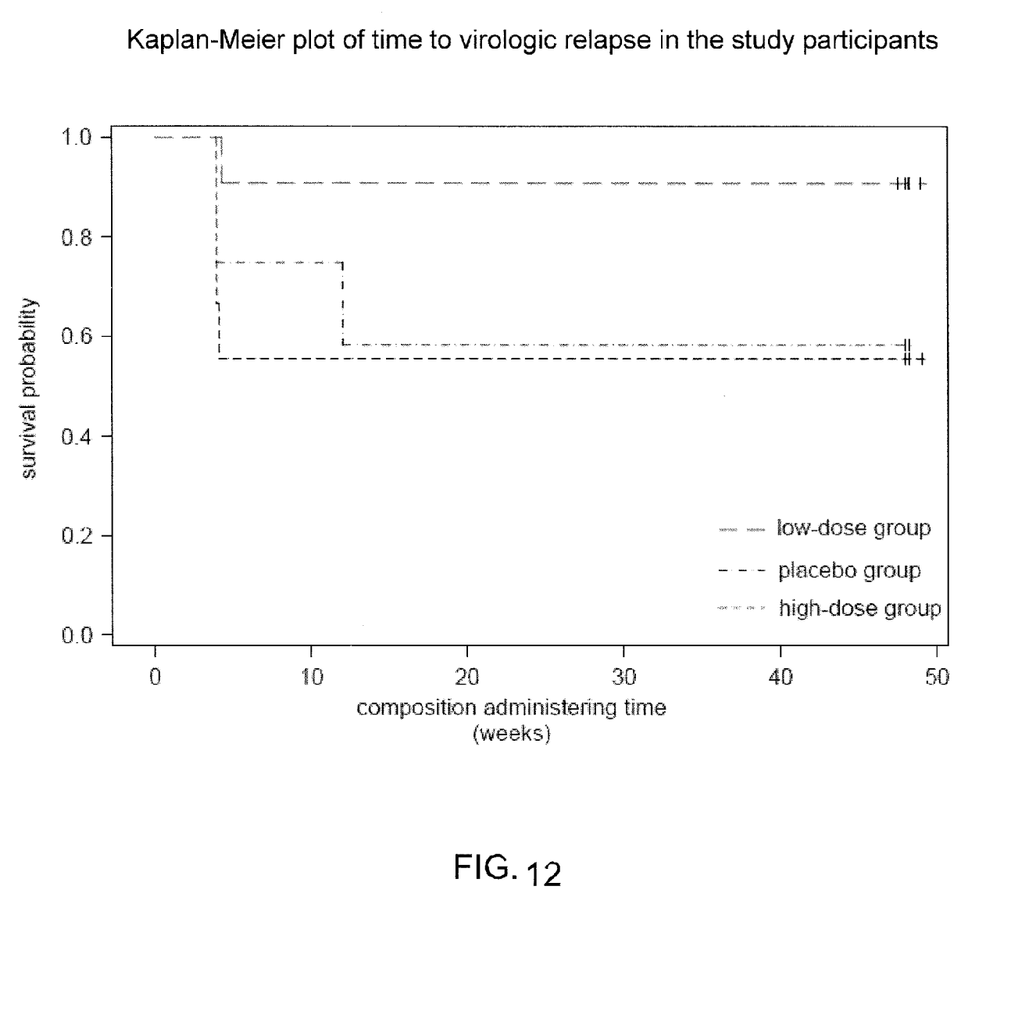
FIG. 12 shows a Kaplan-Meier plot of hepatitis recurrence rate in the participants in the 3 treatment groups (low dose IFN, high dose IFN and placebo).
Figure 13:
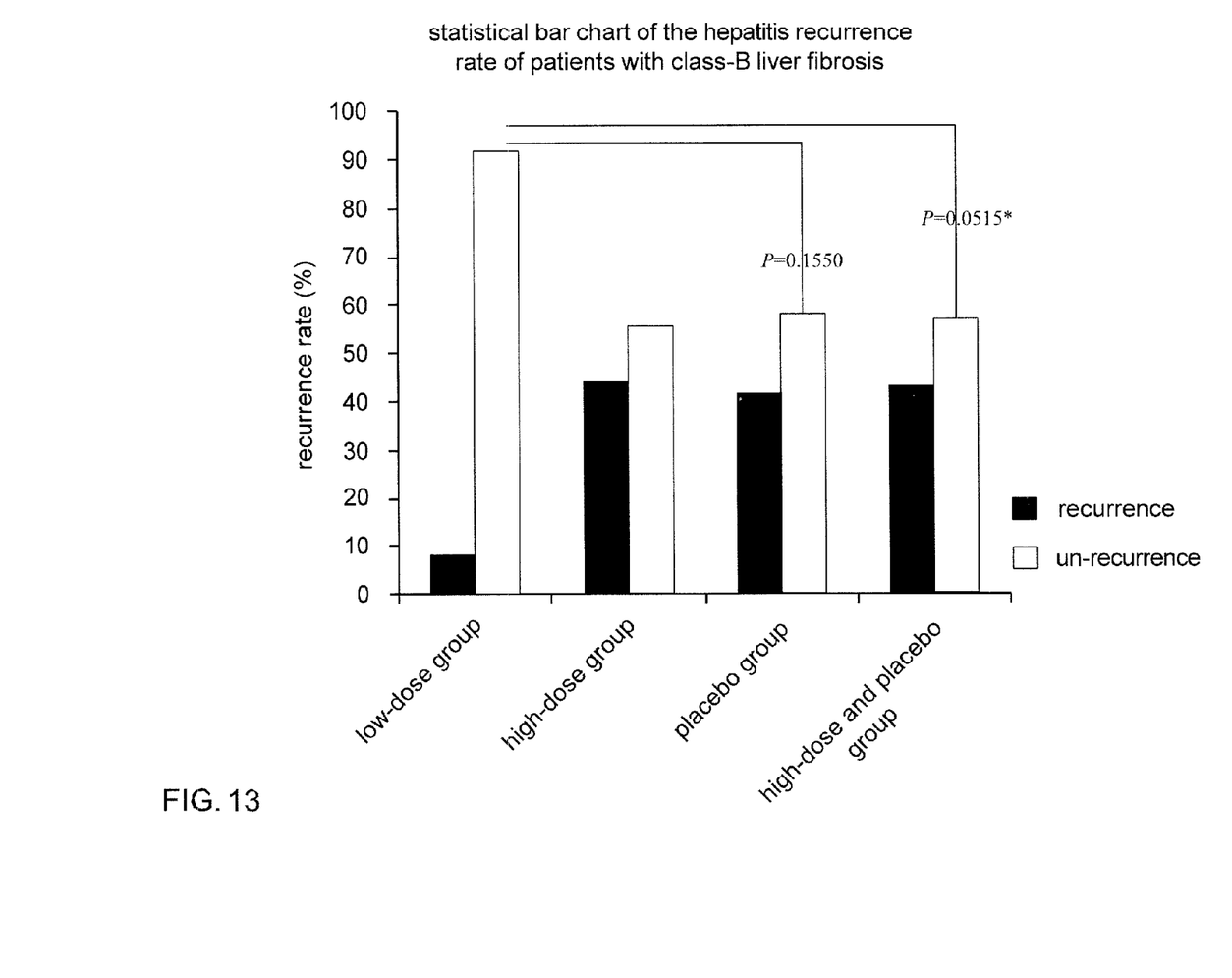
FIG. 13 shows a statistical bar chart of hepatitis recurrence rate in the participants in the 3 treatment groups with Class B liver fibrosis (low dose IFN, high dose IFN and placebo).

FIGS. 12 and 13 respectively show a Kaplan-Meier plot and a statistical bar chart of hepatitis recurrence rates of the participants in the 3 groups. In FIG. 12, the 3 Kaplan-Meier curves reveal that the non-recurrence probability of the participants in the low-dose group is higher and more stable than the participants in the high-dose group and the placebo group. Moreover, FIG. 13 shows that the non-recurrence rate of the participants in the low-dose group is greater, particularly when the participants in the high-dose group and the placebo group are combined as patients who received a "non-effective" dose of IFN.

In summary, the present invention has the following advantages:

1. The clinical trial results prove that an interferon composition consisting of two type I interferons, IFN-α2b and IFN-α8a is able to reduce the viral hepatitis recurrence rate of patients suffering with class-B liver fibrosis.

2. The clinical trial results also prove that the interferon composition of the present invention is capable of enhancing the platelet count of patients infected with hepatitis C virus (HCV) of genotype 1b who have been treated by pegylated IFN in combination with Ribavirin for reducing viral load.

3. Furthermore, the clinical trial results also prove that the interferon composition of the present invention is able to improve the social function of hepatitis patients.

What is claimed is:

1. A method of enhancing the platelet count of a patient having thrombocytopenia, the method comprising:
   identifying a patient with platelet blood levels of less than 150,000 platelets per microliter,
   wherein the normal level of blood platelets in the patient is at or above 150,000 platelets per microliter, and
   orally administering a daily dosage of about 500 IU of interferon-alpha to the patient to stimulate a more rapid increase of blood platelets to a normal level of blood platelets in the patient.

2. The method of claim 1, wherein the patient is infected with hepatitis C virus.

3. The method of claim 1, wherein the thrombocytopenia is due to a reduction of blood platelets in the patient receiving intravenous interferon.

4. The method of claim 1, wherein the interferon-alpha is orally administered bucally.

5. The method of claim 1, wherein the interferon-alpha comprises a first interferon-alpha and a second interferon-alpha.

6. The method of claim 5, wherein the first interferon-alpha is an interferon-$\alpha 2b$ and the second interferon-alpha is an interferon-$\alpha 8a$.

7. The method of claim 5, wherein the ratio of the first interferon-alpha to the second interferon-alpha is 3:1.

8. The method of claim 1, wherein the interferon-alpha is formulated in a liquid or a saliva-soluble lozenge dosage form.

9. The method of claim 8, wherein the interferon-alpha is formulated as the saliva-soluble lozenge dosage form, and orally administering the interferon-alpha comprises:
   introducing the saliva-soluble lozenge dosage form into the mouth of the patient;
   allowing the saliva-soluble lozenge dosage form to dissolve in the patient's mouth to form an interferon-containing solution; and
   contacting the interferon-containing solution with the oral mucosa and the pharyngeal mucosa of the patient.

* * * * *